US007186507B2

(12) United States Patent
Bacallao et al.

(10) Patent No.: US 7,186,507 B2
(45) Date of Patent: Mar. 6, 2007

(54) FLUORESCENT IN SITU RT-PCR

(75) Inventors: Robert Bacallao, Indianapolis, IN (US); Rajesh Kher, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 10/149,461

(22) PCT Filed: Dec. 7, 2000

(86) PCT No.: PCT/US00/33460

§ 371 (c)(1),
(2), (4) Date: Sep. 18, 2002

(87) PCT Pub. No.: WO01/42507

PCT Pub. Date: Jun. 14, 2001

(65) Prior Publication Data

US 2003/0059801 A1    Mar. 27, 2003

Related U.S. Application Data

(60) Provisional application No. 60/169,750, filed on Dec. 9, 1999.

(51) Int. Cl.
C12Q 1/68 (2006.01)
C12P 19/34 (2006.01)
C07H 21/04 (2006.01)

(52) U.S. Cl. .................. 435/6; 435/91.21; 536/24.33

(58) Field of Classification Search .............. 435/6, 435/5, 7.1, 7.9, 91.2, 7.5, 91.21; 536/23.1, 536/24.3, 24.32, 24.33, 22.1; 530/350, 300
See application file for complete search history.

(56) References Cited

U.S. PATENT DOCUMENTS

| | | | |
|---|---|---|---|
| 4,999,293 A | 3/1991 | Barsomian et al. | |
| 5,538,871 A | 7/1996 | Nuovo et al. | |
| 5,804,383 A * | 9/1998 | Gruenert et al. ............... | 435/6 |
| 5,853,697 A | 12/1998 | Strober et al. | |
| 5,962,477 A * | 10/1999 | Mak ......................... | 514/327 |
| 5,989,873 A | 11/1999 | Vinayagamoorthy et al. | |
| 6,218,523 B1 * | 4/2001 | French et al. ............... | 536/23.1 |
| 6,270,966 B1 * | 8/2001 | Weinstein et al. ............ | 435/6 |
| 6,451,530 B1 * | 9/2002 | Hawkins ....................... | 435/6 |

OTHER PUBLICATIONS

Jena et al in "PCR Based RFLP (PBR) as Genetic Marker for Hybrid Rice Improvement" Plant and Animal Genome V Conference, Jan. 12-16, 1997.*
Stratagene Catalog. cDNA synthesis kit. Stratagene Catalog, p. 123, 1995.*
Bagasra et al. Application of in situ PCR techniques to human tissues. PCR3—PCR in situ hybridization a practical approach. pp. 117-138, 1998.*
Vazquez et al. Enhancement of PCRs by partial restriction digestion of genomic templates. Biotechniques, Vo. 26 (1), pp. 9 95, 1999.*
Salian et al. Polymerase chain reaction to detect mycobacterium tuberculosis in histological specimens. Am J Respir Crit Care Med., vol. 158, pp. 1150-1155, 1998.*
Stratagene Catalog. Methylases. Stratagene Catalog, p. 305, 1995.*
Neumaier M, et al. Fundamentals of quality assessment of molecular amplification methods in clinical diagnostics. Clin Chem., vol. 44 (10, p. 12-26, 1998.*
Garner SC, et al. Quantitative analysis of the calcium-sensing receptor messenger RNA in parathyroid adenomas. Surgery, vol. 122 (6), p. 1166-1175, 1997.*
Bagastra et al., "Detection of Human Immunodeficiency Virus Type I Provirus in Mononuclear Cells by *in situ* Polymerase Chain Reaction," *New Engl. J. Med.*, 326:1385-91 (1992).
Boshoff et al., "Kaposi's Sarcoma-Associated Herpesvirus Infects Endothelial and Spindle Cells," *Nature Medicine*, 1:1274-1278 (1995).
Chen et al., "The Use of Granzyme A as a Marker of Heart Transplant Rejection in Cyclosporine or Anti-CD4 Monoclonal Antibody-Treated Rats," *Transplantation*, 55:146-153 (1993).
Chiu et al., "Intracellular Amplification of Proviral DNA in Tissue Sections Using the Polymerase Chain Reaction," *Journal of Histochemistry & Cytochemistry*, 40:333-341 (1992).
Embleton et al., "In-Cell PCR from mRNA: Amplifying and Linking the Rearranged Immunoglobulin Heavy and Light Chain V-Genes with Single Cells," *Nucleic Acids Research*, 20:3831-3834 (1992).
Ertsey and Scavo, "Coverslip Mounted-Immersion Cycled *in situ* RT-PCR for the Localization of mRNA in Tissue Sections," *Biotechniques*, 24:92, 94, 96, 98-100 (1998).
Fleming, "Analysis of Viral Pathogenesis by in situ Hybridization," *Journal of Pathology*, 166: 95-96 (1992).
Haase et al., "Amplification and Detection of Lentiviral DNA Inside Cells," *Proc. Nat'l Acad. Sci. USA*, 87:4971-4975 (1990).
Heniford et al., "Variation in Cellular EGF Receptor mRNA Expression Demonstrated by *in situ* Reverse Transcriptase Polymerase Chain Reaction," *Nucleic Acids Research*, 21:3159-3166 (1993).
Komminoth et al., "Evaluation of Method for Hepatitis C Virus Detection in Archival Liver Biopsies: Comparison of Histology, Immunohistochemistry, In-situ Hybridization, Reverse Transcriptase Polymerase Chain Reaction (RT-PCR) and In-situ RT-PCR," *Pathology, Research & Practice*, 190:1017-1025 (1994).
Kuo et al., "Identification and Characterization of an RNA Specific Primer for Human Tumor Necrosis Factor Receptor-1 (TNFR-1)," *Biochem. & Mol. Biol. Intern'l*,40:119-125 (1996).
Lee et al., "Detection of Soluble Fas mRNA Using In-situ Revers Transcription-Polymerase Chain Reaction," *Laboratory Investigation*, 78:453-459 (1998).

(Continued)

*Primary Examiner*—Suryaprabha Chunduru
(74) *Attorney, Agent, or Firm*—Alice O. Martin; Barnes & Thornburg LLP

(57) ABSTRACT

The present invention describes an in situ reverse transcriptase PCR method in which the background fluorescence is greatly reduced as compared to traditional in situ PCR.

35 Claims, 2 Drawing Sheets

OTHER PUBLICATIONS

Long et al., "Comparison of Indirect and Direct In-situ Polymerase Chain Reaction in Cell Preparations and Tissue Sections: Detection of Viral DNA, Gene Rearrangements and Chromosal Translocations," *Histochemistry*, 99:151-162 (1993).

Martinez et al., "Non-Radioactive Localization of Nucleic Acids by Direct In situ PCR and In-situ RT-PCR in Paraffin-Embedded Sections," *J. Hist. & Cytochem.*, 43:739-747 (1995).

Mee et al., "Quantification of Vitamin D Receptor mRNA in Tissue Sections Demonstrates the Relative Limitations of In situ-Reverse Transcriptase-Polymerase Chain Reaction," *J. Path.*, 182:22-28 (1997).

Negro et al., "Detection of Intrahepatic Replication of Hepatitis C Virus RNA by in situ Hybridization and Comparison with Histopathology," *Proc. Nat'l Acad. Sci. USA*, 89:2247-2251 (1992).

Nuovo et al., "An Improved Technique for the in situ Detection of DNA after Polymerase Chain Reaction Amplification," *A.J. Path.*, 139:1239-1244 (1991).

Nuovo et al., "In situ Localization of PCR-Amplified Human and Viral cDNAs," *Genome Research*, 2:117-23 (1992).

Nuovo, "PCR In situ Hybridization," *Methods in Molecular Biology*, 33:223-241 (1994).

Nuovo, "The Nonspecific Pathways of PCR," in *PCR in situ Hybridization: Protocols and Applications*, 2nd ed., Lippincott-Raven, Philadelphia, pp. 54-99, 1996.

O'Leary et al., "In situ PCR: Pathologist's Dream or Nightmare?," *Journal of Pathology*, 178:11-20 (1996).

Patterson et al., "Detection of HIV-1 DNA and Messenger RNA in Individual Cells by PCR-Driven *in Situ* Hybridization and Flow Cytometry," *Science*, 260:976-979 (1993).

Patel et al., "Detection of Epidermal Growth Factor Receptor mRNA in Tissue Sections from Biopsy Specimens Using *in Situ* Polymerase Chain Reaction," *American Journal of Pathology*, 144:7-14 (1994).

Peters et al., "Detection of Rare RNA Sequences by Single-Enzyme *in Situ* Reverse Transcription Polymerase Chain Reaction: High Resolution Analyses of Interleukin-6 mRNA in Paraffin Sections of Lymph Nodes," *American Journal of Pathology*, 150:469-476 (1997).

Singer et al., "Detection of HIV-1-Infected Cells from Patients Using Nonisotopic *in Situ* Hybridization," *Blood*, 74: 2295-2301 (1989).

Staecker et al., "A Procedure for RT-PCR Amplification of mRNAs in Histological Specimens," *Biotechniques*, 16:76-80 91994).

Tecott et al., "*In Situ* Transcription: Specific Synthesis of Complementary DNA in Fixed Tissue Sections," *Science*, 240:1661-1664 (1988).

Tolker-Nielsen et al., "Non-Genetic Population Heterogeneity Studies by *in Situ* Polymerase Chain Reaction," *Molecular Microbiology*, 27:1099-1105 (1998).

\* cited by examiner

FLUORESCENT IN SITU RT-PCR

The present application claims priority to copending priority U.S. Provisional Application No. 60/169,750 which was filed Dec. 9, 1999.

The U.S. Government may have rights in the present invention pursuant to the terms of grant numbers NIH-NIDDK ROI DK 46883-06A1 and NIH-NIDDK R29 DK 46883-05 awarded by the National Institutes of Health.

FIELD OF THE INVENTION

The present invention relates to molecular biology techniques. More particularly, the invention is directed to novel methods and compositions for performing in situ RT-PCR.

BACKGROUND OF THE INVENTION

A variety of molecular biology techniques can be used to detect RNAs. Hybridization of nucleic acid probes to complementary RNA after electrophoretic separation is used extensively in the analysis of gene structure, expression and diagnostic tests (Fleming, *Journal of Pathology*, 166(2), 95–6, 1992; Singer et al, *Blood*, 74(6), 2295–301, 1989). These techniques require technically demanding generation of the antisense RNA probe, and denaturing gels that may contain harmful chemicals such as formaldehyde. Additionally these methods do not allow the precise cellular localization of the RNA target. In situ hybridization (ISH) permits the localization of specific nucleic acid sequences at the cellular level and detection of gene expression frequencies. However, the method though highly specific may often be overshadowed by a relatively low detection sensitivity (Chen et al., *Transplantation*, 55(1), 146–53, 1993; Martinez et al., *J. Hist. & Cytochem.*, 43(8), 739–47, 1995).

Amplification of the target mRNAs by PCR is used to improve sensitivity enabling detection of low abundancy mRNAs in a given cell (Chen et al., *Transplantation*, 55(1), 146–53, 1993; Tecott et al, *Science*, 240(4859), 1661–4 1988; Nuovo et al., *A. J. Path.*, 139(6), 1239–44, 1991; Bagasra et al., *New Engl. J. Med.*, 326(21), 1385–91, 1992; Patterson et al., *Science*, 260(5110), 976–9, 1993; Staecker et al., *Biotechniques*, 16(1), 1994; Chiu. et al., *Journal of Histochemistry & Cytochemistry*, 40(3), 333–41, 1992; Heniford, et al., *Nucleic Acids Research*, 21(14), 3159–66, 1993; Nuovo et al., *Genome Research*, 2(2), 117–23, 1992; Peters et al., *American Journal of Pathology*, 150(2), 469–76, 1997; Tolker-Nielsen et al., *Molecular Microbiology*, 27(6), 1099–105; 1998; Lee et al., *Laboratory Investigation*, 78(4), 453–9, 1998). Various detection methods have been used following target mRNA amplification in tissue sections or cell suspensions (Chen et al., *Transplantation*, 55(1), 146–53, 1993; Nuovo et al., *A. J. Path.*, 139(6), 1239–44, 1991; Staecker et al., *Biotechniques*, 16(1), 1994; Peters et al., *American Journal of Pathology*, 150(2), 469–76, 1997; Tolker-Nielsen et al., *Molecular Microbiology*, 27(6), 1099–105; 1998; Lee et al., *Laboratory Investigation*, 78(4), 453–9, 1998; Patel, et al., *American Journal of Pathology*, 144(1), 7–14; 1994; Haase, et al., *Proc. Nat'l Acad. Sci. USA*, 87(13), 4971–5, 1990; Negro et al., *Proc. Nat'l Acad. Sci. USA*, 89(6), 2247–51, 1992).

RT-PCR followed by a separate ISH step using either a radiolabeled or non-isotopically labeled complementary probe for detection and localization of the target mRNAs is quite cumbersome (Mee, et al., *J. Path.*, 182(1), 22–8, 1997; Ertsey and Scavo, *Biotechniques*, 24(1), 92, 94, 96, 98–100, 1998).

Alternatively, direct incorporation of a labeled deoxynucleotide in the amplification step can be used (Chen et al., *Transplantation*, 55(1), 146–53, 1993; Martinez et al., *J. Hist. & Cytochem.*, 43(8), 739–47, 1995; Heniford, et al., *Nucleic Acids Research*, 21(14), 3159–66, 1993; Patel, et al., *American Journal of Pathology*, 144(1), 7–14; 1994; Boshoff et al., *Nature Medicine*, 1(12) 1274–8, 1995). However, direct incorporation of the labeled dNTP results in a high background from nonspecific amplification following mis-printing (extension of primers annealed to non-target sequences) (O'Leary et al., *Journal of Pathology*, 178(1), 11–20, 1996; Long et al., *Histochemistry*, 99(2), 151–62, 1993). Hot-start PCR (Nuovo, PCR in situ Hybridization: Protocols and Applications. Lippincott-Raven, Philadelphia, pp. 54–99, 1996) and the use of labeled primers in PCR (Embleton et al., *Nucleic Acids Research*, 20(15), 3831–7, 1992) instead of direct incorporation of labeled deoxynucleotide helps in eliminating background due to mis-printing or due to primer-independent events. The use of labeled primers across the intron-exon junctions may also circumvent the problems of non-specific amplification from genomic DNA (Lee et al., *Laboratory Investigation*, 78(4), 453–9, 1998; Kuo et al., *Biochem. & Mol. Biol. Intern'l*, 40(1), 119–25, 1996). In spite of DNase I pretreatment of the samples (Martinez et al., *J. Hist. & Cytochem.*, 43(8), 739–47, 1995; Tolker-Nielsen et al., *Molecular Microbiology*, 27(6), 1099–105; 1998; Ertsey and Scavo, *Biotechniques*, 24(1), 92, 94, 96, 98–100, 1998; Nuovo, *Meth. Mol. Biol.*, 33:223–41, 1994) and hot-start modification (Nuovo, PCR in situ Hybridization: Protocols and Applications. Lippincott-Raven, Philadelphia, pp. 54–99, 1996), non-specific amplification from undigested genomic DNA still remains a severe drawback in presently available methods (Komminoth et al., *Path. Res. & Pract.*, 190(11), 1017–25, 1994), especially in cases where genomic sequence data is incomplete.

SUMMARY OF THE INVENTION

The present invention describes method of in situ RT PCR with increased specificity and rapid in situ detection of cellular mRNAs and thus may be used for pathological diagnosis.

In preferred embodiments, the present invention describes a method for in situ amplification of a target nucleic acid in a selected cell comprising contacting a fixed, permeabilized cell with a restriction endonuclease composition comprising at least one restriction endonuclease to produce a restriction digest; contacting the cell with a DNase to produce a DNase digested cell; incubating the cell with a reverse transcriptase (RT) cocktail comprising an RT enzyme and a RT primer(s) specific for the target nucleic acid to produce a cDNA; and amplifying the cDNA using a PCR reaction in the presence of forward and reverse PCR primers specific for the target nucleic acid wherein at least one of the PCR primers is labeled.

In preferred embodiments, the PCR primers are labeled with a radioactive label, an immunocytochemical label or a fluorescent label to facilitate detection of the amplified cDNA. In particularly preferred embodiments, the fluorescent label fluoresces in the far red range of fluorescence range, e.g., about 500 nm or greater, or about 500 nm to 700 nm, or about 545 nm or higher, or about 645 nm or higher. More specifically, the label may be selected from the group consisting of Cy-5, Cy-3, rhodamine and Texas Red. In other embodiments, the primer is labeled with biotin and digoxigenin.

In preferred embodiments, the restriction endonuclease composition comprises one or more tetra-cutter restriction endonucleases. More particularly, the restriction endonuclease composition comprises one or more restriction endonucleases selected from the group consisting of Hae III, Hpa II, Mbo I, Cfo I Hha I, and Bst 98 I. In other embodiments, the DNase is DNase I. In particular embodiments, the proteinase is selected from the group consisting of trypsinase, pepsinogen, and proteinase K.

The reverse transcriptase may be any RT commonly used in an RT PCR reaction. In exemplary embodiments, the reverse transcriptase is selected from the group consisting of Superscript™; AMV Reverse Transcriptase, M-MLV Reverse Transcriptase, Retrotherm™; Thermoscript™ and Tth reverse transcriptase.

In specific embodiments, the cell may be from a tissue sample selected from the group consisting of kidney, heart, lung, liver, blood, pancreas, cervix, breast and muscle. Of course these are only exemplary and the ISRT-PCR reaction may be used in any tissue amenable to be analysis via a histological method. In preferred embodiments, the tissue sample is obtained from a subject. Such a subject may be one that has a disease selected from the group consisting of cancer, cystic fibrosis, cardiac hypertrophy, and autoimmune diseases. In preferred embodiments, the cell is a tumor cell.

In particular embodiments, the target nucleic acid encodes a marker for an infectious particle. The infectious particle may be a viral particle selected from the group consisting of hepatitis A, hepatitis B, hepatitis C, HIV 1, HIV 2, and Epstein-Barr virus particles. Alternatively the infectious particle may be a bacterial particle such as *M. tuberculin*, or *M avian*. In particular embodiments, the target nucleic acid is a disease specific nucleic acid. More specifically the target nucleic acid may be selected from the group consisting of Muc1, CCAM, RB, APC, DCC, MEN-I, MEN-II, zac1, MMAC1, FCC, MCC p16, p21, p27, p53, p73, zac1, MMAC1, Rb, WT-1, DCC, NF-1, NF-2, BRCA-1, BRCA-2, MTS, CA125, prostate specific antigen, melanoma antigen gp75, CD9, CD63, CD53, CD37, CD63, R2, CD81, CO029, TI-1, L6 and SAS.

In some embodiments, the cells are fixed in a fixative selected from the group consisting of formaldehyde, formalin, paraformaldehyde and glutaraldehyde. It should be understood that these are merely exemplary fixatives and those of skill in the art will know of other fixatives that may be used to fix histological slides. In particular embodiments, the fixed cells are located in a histochemical section affixed to a microscope slide.

The cells may also be permeabilized using any method known in the art. For example, the fixed cell may be contacted with a proteinase to produce a permeabilized cell. Also, the RT and PCR reactions may be carried out using any methods and conditions known in the art. If desired, either the forward or the reverse PCR primer used during the PCR reaction can be the same RT primer used for reverse transcription.

In specific embodiments, the method further may comprise detecting the amplified nucleic acid. In preferred embodiments, the PCR amplification reaction employs a DNA polymerase selected from the group consisting of DNA Polymerase I, T4 DNA Polymerase, DNA Polymerase I Klenow fragment, PLATNUM taq™, Tfl DNA Polymerase, Taq DNA Polymerase, Tli DNA Polymerase, Tth DNA Polymerase, Vent™, Deepvent™ and pfu. In other embodiments, the cell comprises between about 0.1 picograms and 10 micrograms of poly (A)+RNA. In other defined embodiments, the cell comprises between 1 and $10^8$ copies of the poly(A)+RNA.

In other specific embodiments, the method further may comprise the step of counterstaining the cell with a nonfluorescent dye to aid in identification of the cell.

Also contemplated is a method for in situ amplification of a target nucleic acid in a selected cell comprising contacting a fixed, permeabilized cell with a restriction endonuclease composition comprising Sau 96I or Hae III to produce a restriction digest; contacting the restriction digest with a DNase to produce a DNase digested cell; incubating the DNase digested cell with a reverse transcriptase (RT) cocktail contacting an RT enzyme and RT primer(s) specific for the target nucleic acid to produce a cDNA; and amplifying the cDNA using a polymerase chain reaction (PCR) reaction in the presence of forward and reverse PCR primers specific for the target nucleic acid wherein at least one of the PCR primers is labeled to facilitate detection wherein the contacting of the digested cell with the reaction endonuclease composition produces an increased and specific signal for detection as compared to an in situ RT PCR reaction conducted in the absence of the restriction endonuclease composition. In specific embodiments, the restriction endonuclease composition comprises a further restriction endonuclease selected from the group consisting of Hae III, Hpa II, Mbo I, Cfo I Hha I, and Bst 98 I.

An additional aspect of the present invention provides a method for improving the signal from an in situ RT PCR reaction comprising subjecting the nucleic acids of the fixed cell to a restriction endonuclease reaction and a DNase digestion. Preferably said restriction endonuclease digestion is carried out prior to DNase digestion. Another aspect of the present invention provides a method for improving the signal from an in situ RT PCR reaction comprising carrying out PCR using at last one PCR primer labeled with a fluorescent label that fluoresces in the far red range.

Also provided is a kit for use in in situ RT PCR, the kit comprising discrete containers of a first restriction endonuclease, a second restriction endonuclease, and an RNase free DNase. The kit may further comprise a reverse transcriptase. In other independent embodiments, the kit may further include a DNA polymerase. The first restriction endonuclease may be selected from the group consisting of Hae III, Hpa II, Mbo I, Cfo I Hha I, and Bst 98 I. In other embodiments, the second restriction endonuclease is selected from the group consisting of Hae III, Hpa II, Mbo I, Cfo I Hha I, and Bst 98 I.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Krtk expression in metanephric mesenchyme in 11.5 day mouse embryonic kidney grown in organ culture for 9 days (DNAse positive, RT positive). This signal is specific for the cytoplasmic mRNA coding for krtk. FIG. 1B. Preferential expression in proximal tubules, lower expression in distal tubules and no expression in glomerulus in adult mouse kidney section (DNAse positive, RT positive). FIG. 1C. Positive control for krtk primers (DNASE negative RT positive). This signal includes nuclear genomic signals in addition to the mRNA. FIG. 1D. Negative control for krtk primers DNAse positive RT negative). Note the lack of staining when a reverse transcription reaction is not performed. This eliminates the possibility that the signal was due to autofluorescence. FIG. 1E. Positive control for the method using standard primers for GAPDH (DNAse positive, RT positive).

FIG. 2A: Background fluorescence, no RT-PCR reaction. FIG. 2B: Krtk primers only, no reverse transcriptase in the reverse transcription reaction. FIG. 2C: RT-PCR performed without Taq polymerase. FIG. 2D: DNase I treated, reverse transcriptase positive, in situ PCR. Image of renal proximal tubules. Note the extensive cytoplasmic staining and the absence of nuclear staining due to the DNase I and restriction enzyme treatment. FIG. 2E: DNase I treated, reverse transcriptase positive, in situ PCR in a kidney section. Increased staining is noted in a proximal tubule segments (P) as compared to the distal tubules (D). Punctate staining in the glomerulus (G) is due to red blood cells. FIG. 2F: Direct in situ RT-PCR using primers specific for GAPDH. In contrast to the differential expression of krtk in murine kidney, GAPDH expression is similar in all nephron segments. FIG. 2G. Direct in situ PCR using GAPDH primers. Samples was digested with DNase I but not treated with restriction enzymes. Note diffuse staining throughout the cells. No nuclear compartment is discernable. Signal intensity in the nucleus is equivalent to the cytoplasmic signal.

DETAILED DESCRIPTION OF THE PREFERRED EMBODIMENTS

Figures 1A, 1B, 1C, 1D, 1E:
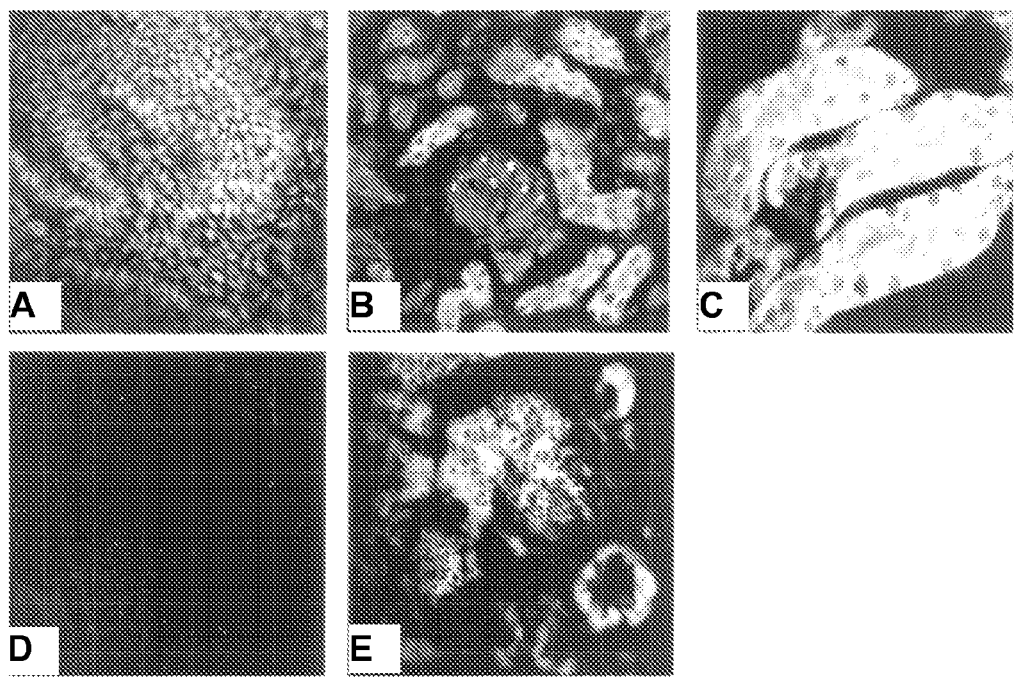
FIGS. 1A–1E. In situ RT PCR with krtk specific primers.

Prior attempts to perform in situ reverse transcription-polymerase chain reaction (ISRT-PCR) using fluorescent labeling methods have not been successful due to problems associated with endogenous fluorescence in the tissue and high background labeling of the tissue with the fluorescent probes. These deficiencies made experimental results uninterpretable.

In the present invention, ISRT-PCR is employed in a highly modified version to address the problem of non-specific background amplification by pretreatment of samples with an enzyme that cuts the target genomic sequence delineated within the primers and/or any tetracutter restriction enzyme(s) in conjunction with DNAse before RT-PCR. This novel approach coupled with the use of a sense primer tagged with a far-red shifted dye such as Cy-5 in the PCR step allows identification of the target mRNAs by fluorescence microscopy. Without compromising on the sensitivity, the method provides increased specificity, is rapid and can allow image analysis of confocal microscopic images for analysis and estimation of accumulated labeled cDNA.

The direct fluorescence labeling method of the present invention eliminates the in situ hybridization step that is required in the prior art in situ RT PCR methods (Tecott et al., *Science*, 240(4859), 1661–4 1988; Embleton et al., *Nucleic Acids Research*, 20(15), 3831–7, 1992; Ray, et al., *Mod. Pathol.*, 4, 124A, 1991). In the prior art method, the in situ hybridization step uses a radioactive probe and the resultant x-ray micrograph was overlaid onto a photomicrograph to correlate transcript expression with tissue localization. By contrast, in the present invention, at the end of labeling method, the fluorescent signal is directly imaged in the tissue section. Fluorescent signals are simultaneously co-localized with phase contrast photomicrographs, when a tissue stain, such as hematoxylin is used to counter-stain tissue sections. An additional advantage of direct in situ RT-PCR described in this invention is the improved signal-to-noise ratio of labeled specimens as compared to negative controls or unlabeled samples.

The increased signal strength and signal specificity that is an advantage of this invention is achieved by overcoming two obstacles that are found in the prior existing techniques for RT-PCR. First, tissue sections have significant autofluorescence when imaged with excitation and emission filters optimized for fluorescein and rhodamine. The inventors discovered that this endogenous fluorescent signal was markedly attenuated at longer emission wavelengths. At an emission wavelength of 645 nm, which is the emission maximum for Cy-5, tissue sections had little to no detectable endogenous fluorescence. Texas Red also could be used as an alternatively fluorescent probe although at this emission wavelength (545 nm). The reduced background fluorescence improved the interpretation of fluorescence signals and analysis of signal specificity.

The second problem identified by the inventors was the contribution of residual genomic DNA to the images. Intense nuclear staining was observed in samples without prior DNase I treatment. DNase I pretreatment of samples (Martinez et al., *J. Hist. & Cytochem.*, 43(8), 739–47, 1995; Tolker-Nielsen et al., *Molecular Microbiology*, 27(6), 1099–105; 1998; Ertsey and Scavo, *Biotechniques*, 24(1), 92, 94, 96, 98–100, 1998; Nuovo et al., *Genome Research*, 4(2), 89–96, 1994) did not eliminate non-specific amplification from undigested genomic DNA (Komminoth et al., *Pathology, Research & Practice*, 190(11), 1017–25, 1994). The inventors found that DNase I treatment alone did not eliminate nuclear labeling entirely. In order to improve the specificity of labeling, the inventors found that adding a specific restriction enzyme digestion step to the experimental protocol, followed by DNase I digestion eradicates nuclear staining in samples in which a reverse transcriptase reaction or RT-PCR reaction was performed. Further, the inventors found that restriction enzymes that cut within the DNA sequence bracketed by the chosen PCR primers appeared to work better than enzymes that did not specifically cut within the targeted genomic DNA sequence.

In the past direct incorporation of a labeled deoxynucleotide in the amplification step in PCR has been used for detection of target mRNAs in cells or tissue sections (Martinez et al., *J. Hist. & Cytochem.*, 43(8), 739–47, 1995; Heniford, et al., *Nucleic Acids Research*, 21(14), 3159–66, 1993; Patel, et al., *American Journal of Pathology*, 144(1), 7–14; 1994; Boshoff et al., *Nature Medicine*, 1(12) 1274–8, 1995; Chen and Fuggle, *Am. J. Pathol.*, 143(6), 1527–34, 1993). However, direct incorporation of the labeled dNTP has been reported to result in a high background from non-specific mis-primed amplification (O'Leary et al., *Journal of Pathology*, 178(1), 11–20, 1996; Long et al., *Histochemistry*, 99(2), 151–62, 1993). The use of Cy-5 labeled 5'-primer in the PCR step eliminates this potential problem very effectively.

The improved specificity of direct in situ RT-PCR and the elimination of a time consuming in situ hybridization step in this protocol should extend the utility of this method. Potentially, direct in situ RT-PCR may be employed to extend the accuracy of cancer diagnosis in biopsy specimens. Additionally, since fluorescent signals are easily quantified it is possible to automate sample processing and identification of positively labeled specimens.

In summary, the inventors have developed a method of in situ RT-PCR that is highly specific and enables investigators to identify the sites of RNA transcript production in tissues. This method eliminates the in situ hybridization step found in prior descriptions of in situ RT-PCR. This improvement in mRNA detection and relative ease of sample preparation may increase the use of this method in pathological diagnosis. Methods and compositions describing for making and using the claimed invention are described in further detail.

A. In Situ RT PCR

The present invention describes a method for in situ amplification of a target nucleic acid in a selected cell comprising fixing the selected cell; contacting the fixed cell with a proteinase to produce a permeabilized cell; contacting the permeabilized cell with a restriction endonuclease composition comprising at least one restriction endonuclease to produce a restriction digest; contacting the restriction digest with a DNase to produce a DNase digested cell; incubating the cell with a reverse transcriptase (RT) cocktail comprising an RT enzyme and RT primer(s) specific for the target nucleic acid to produce a cDNA; and amplifying the cDNA using a PCR reaction in the presence of forward and reverse PCR primers specific for the target nucleic acid wherein at least one of the PCR primers is labeled.

Methods of cell fixation for use in RT-PCR are well known to those of skill in the art. In a preferred embodiment, the tissues are fixed in paraformaldehyde-sucrose solution. However, this is merely an exemplary fixative and examples of such cell fixation may be found in, for example, Haase et al., (*Proc. Natl. Acad. Sci.* USA 87, 4971–4975, 1990), Bagasra et al., (*New Engl. J. Med.* 326, 1,385–391 1992); U.S. Pat. No. 5,830,663; U.S. Pat. No. 5,538,871; U.S. Pat. No. 5,589,333; U.S. Pat. No. 5,364,790; U.S. Pat. No. 5,681,741; U.S. Pat. No. 5,750,347.

In particular aspects of the present invention the primers are labeled with a radioactive label, an immunocytochemical label or a fluorescent label to facilitate detection of said amplified cDNA. The preferred label is Cy-5, however, other probes that are envisioned to be useful are Cy-3, rhodamine and Texas Red. In certain embodiments, the primer may be labeled with biotin, digoxigenin which may subsequently be detected using binding assays well known to those of skill in the art. Additional labels that will be useful in conjunction with the present invention will be well known to those of skill in the art. Given the findings described herein it is contemplated that the preferred fluorescent labels will be any label that has an emission wavelength of fluorescence of greater than about 500 nm. Thus the emission wavelength may be between about 500 nm and about 700 nm. Preferably the emission wavelength is greater than 600 nm. More preferably, the emission wavelength is about 645 nm.

In certain embodiments, the cell may be counter-stained with a non-fluorescent dye to aid in identification of the cell. The field of histology employs many such stains that will be useful in this aspect of the present invention. These include but are not limited to hematoxylin, thionin, gentian violet, giemsa blood stain, ethyl green stain and methyl blue. Other histological stains that may be useful will be well known to those of skill in the art. Additional aspects of the ISRT-PCR are described throughout the application.

B. Enzymes and Reagents

The present section provides examples of enzymes and reagents used in the present invention to carry out in situ RT-PCR, these include endonucleases, RT enzymes, DNA polymerases, RNase inhibitors and other compositions required or helpful for optimizing reaction conditions. Of course, the enzymes and reagents discussed below are exemplary and it is understood that any additional enzymes or reagents that possess similar activities may substitute for those specifically described.

a. Restriction Endonucleases

Restriction endonucleases are endonucleases that are capable of recognizing a specific sequence of bases in a DNA molecule and cleaving the DNA strands at specific sites. Many kinds of restriction endonucleases have so far been found. Among them, class II restriction endonucleases, which can recognize specific DNA sequence and digest the DNA strand specifically within the sequence, are especially important and essentially used in genetic engineering techniques.

Restriction endonucleases with low cutting frequencies are particularly convenient for structural analyses of high molecular weight DNA such as genome analysis projects of several living things.

In the present invention, tetra-cutter restriction endonucleases are preferred. Exemplary endonucleases that may be employed in the present invention include but are not limited to Hae III, Hpa II, Mbo I, Cfo I Hha I, Bst 98 I. Additional endonucleases that may be useful in the present invention are well known to those of skill in the art. For example, a source of restriction enzymes well known to those of skill in the art is Promega (Madison, Wis.).

Additional restriction endonucleases that may be useful in the present invention are described in for example ApaLI (U.S. Pat. No. 5,616,484); FSEI (U.S. Pat. No. 5,543,308); SacI (U.S. Pat. No. 5,532,153); SSPI (U.S. Pat. No. 5,516,678); BsoBI (U.S. Pat. No. 5,492,823); NCO I (U.S. Pat. No. 5,202,248); FokI (U.S. Pat. No. 5,487,994); CviJI (U.S. Pat. No. 5,472,872); BglII (U.S. Pat. No. 5,434,068); AATII, ALUI (U.S. Pat. No. 5,405,768); SgfI (U.S. Pat. No. 5,391,487); NotI (U.S. Pat. No. 5,371,006); BGLI (U.S. Pat. No. 5,366,882); DdeI (U.S. Pat. No. 5,354,680); SexAI (U.S. Pat. No. 5,354,669); AluI (U.S. Pat. No. 5,334,526); XhoII (U.S. Pat. No. 5,304,480); Srf I (U.S. Pat. No. 5,300,432); Hpa I (U.S. Pat. No. 5,298,404); NaeI (U.S. Pat. No. 5,292,641); SacII (U.S. Pat. No. 5,288,696); Nla III (U.S. Pat. No. 5,278,060); SPHI (U.S. Pat. No. 5,262,318); APO I (U.S. Pat. No. 5,200,337); Pme I (U.S. Pat. No. 5,196,330); AscI (U.S. Pat. No. 5,192,676); Ssp4800 I (U.S. Pat. No. 5,183,747); SwaI (U.S. Pat. No. 5,158,878); MamI (U.S. Pat. No. 5,153,122); NgoAIII (U.S. Pat. No. 5,147,800); Nde I (U.S. Pat. No. 5,139,942); SgrAI (U.S. Pat. No. 5,134,069); AseI (U.S. Pat. No. 5,100,793); NLAVI (U.S. Pat. No. 5,075,232); FseI (U.S. Pat. No. 5,061,628); MwoI (U.S. Pat. No. 5,053,330); PvuI (U.S. Pat. No. 5,049,501); AFL II (U.S. Pat. No. 5,030,569); Hinc II (U.S. Pat. No. 5,015,581); ACCI (U.S. Pat. No. 5,004,691); XmaI (U.S. Pat. No. 5,002,882); FokI (U.S. Pat. No. 4,999,294); HhaI (U.S. Pat. No. 4,999,293); Eag I (U.S. Pat. No. 4,996,151); FnuDI (U.S. Pat. No. 4,988,620); HgiAI (U.S. Pat. No. 4,987,074); XbaI (U.S. Pat. No. 4,983,542); HinPI (U.S. Pat. No. 4,983,522); KspI (U.S. Pat. No. 4,975,376); Ksp632 I (U.S. Pat. No. 4,970,149); SpII (U.S. Pat. No. 4,886,756); Dsa I (U.S. Pat. No. 4,871,664); Dra II (U.S. Pat. No.

4,840,901); mae III (U.S. Pat. No. 4,693,980); Mae II (U.S. Pat. No. 4,693,979); MaeI (U.S. Pat. No. 4,693,978); XcyI (U.S. Pat. No. 4,588,689). It should be understood that the endonucleases listed here are merely exemplary and any endonuclease that will decrease the non-specific background reading in an ISRT-PCR reaction will be useful in the methods of the present invention. A preferred endonuclease will be one which cuts the target genomic sequence delineated by the primer pairs used.

b. Reverse Transcriptases

Particular aspects of the invention will use reverse transcnptase (RT) enzymes. The following is a list of exemplary RT enzymes that may be useful in the present invention.

M-MLV Reverse Transcriptase. M-MLV (Moloney Murine Leukemia Virus Reverse Transcriptase) is an RNA-dependent DNA polymerase requiring a DNA primer and an RNA template to synthesize a complementary DNA strand. The enzyme is a product of the pol gene of M-MLV and consists of a single subunit with a molecular weight of 71 kDa. M-MLV RT has a weaker intrinsic RNase H activity than Avian Myeloblastosis Virus (AMV) reverse transcriptase which is important for achieving long full-length complementary DNA (>7 kB). M-MLV can be use for first strand cDNA synthesis and primer extensions. Storage is recommended at −20° C. in 20 mM Tris-HCl (pH 7.5), 0.2M NaCl, 0.1 mM EDTA, 1 mM DTT, 0.01% Nonidet® P-40, 50% glycerol. The standard reaction conditions are 50 mM Tris-HCl (pH 8.3), 7 mM $MgCl_2$, 40 mM KCl, 10 mM DTT, 0.1 mg/ml BSA, 0.5 MM $^3$H-dTTP, 0.025 mM oligo$(dT)_{50}$, 0.25 mM poly$(A)_{400}$ at 37° C.

M-MLV Reverse Transcriptase, Rnase H Minus. This is a form of Moloney murine leukemia virus reverse transcriptase (RNA-dependent DNA polymerase) which has been genetically altered to remove the associated ribonuclease H activity (Tanese and Goff, 1988). It can be used for first strand cDNA synthesis and primer extension.

AMV Reverse Transcriptase. Avian Myeloblastosis Virus reverse transcriptase is a RNA dependent DNA polymerase that uses single-stranded RNA or DNA as a template to synthesize the complementary DNA strand (Houts et al., *J. Virol.*, 29:517–522, 1979). It has activity at high temperature (42° C.–50° C.). This polymerase has been used to synthesize long cDNA molecules.

Reaction conditions are 50 mM Tris-HCl (pH 8.3), 20 mM KCl, 10 mM $MgCl_2$, 500 µM of each dNTP, 5 mM dithiothreitol, 200 µg/ml oligo-dT (12–18), 250 µg/ml polyadenylated RNA, 6.0 pMol 32P-dCTP, and 30 U enzyme in a 7 b µl volume. Incubate 45 min at 42° C. Storage buffer is 200 mM $KPO_4$ (pH 7.4), 2 mM dithiothreitol, 0.2% Triton X-100, and 50% glycerol. AMV may be used for first strand cDNA synthesis, RNA or DNA dideoxy chain termination sequencing, and fill-ins or other DNA polymerization reactions for which Klenow polymerase is not satisfactory (Maniatis et al., *Cell*, 8:163, 1976).

Superscript™ II RNase H—Reverse Transcriptase (U.S. Pat. No. 5,244,797, incorporated herein by reference) is purified to near homogeneity from *E. coli* containing the pol gene of Moloney Murine Leukemia Virus. The enzyme is used to synthesize first strand cDNA and will generally give higher yields of cDNA and more full length product than other reverse transcriptases.

An exemplary RT PCR that employs SUPERSCRIPT™ can be found in the Gibco catalog. Briefly, a 20 µl reaction volume can be used for 1–5 µg of total RNA or 50–500 ng of mRNA. The following components are added to a nuclease-free microcentrifuge tube: 1 µl Oligo (dT)12–18 (500 µg/ml) 1–5 µg total RNA, sterile, distilled water to 12 µl. The reaction mixture is heated to 70° C. for 10 min and quickly chilled on ice. The contents of the tube are collected by brief centrifugation. To this precipitate is added: 4 µl 5× First Strand Buffer, 2 µl 0.1 M DTT, 1 µl 10 mM dNTP Mix (10 mM each dATP, dGTP, dCTP and dTTP at neutral pH). The contents are mixed gently and incubate at 42° C. for 2 min. Then 1 µl (200 units) of Superscript II™ is added and the reaction mixture is mixed by pipetting gently up and down. This mixture is then incubated for 50 min at 42° C. and then inactivated by heating at 70° C. for 15 min. The cDNA can now be used as a template for amplification in PCR. However, amplification of some PCR targets (those >1 kb) may require the removal of RNA complementary to the cDNA. RNA complementary to the cDNA may be removed by adding 1 µl (2 units) of *E. coli* RNase H and incubating at 37° C. for 20 min.

Retrotherm™ RT (Epicentre technologies) is a thermostable reverse transcriptase and DNA polymerase derived from a thermophilic bacterium. This thermostable enzyme has both RNA- and DNA-dependent DNA polymerase activities under the same reaction conditions. These characteristics enable researchers to synthesize both strands of a specific cDNA in a single tube with no buffer changes. The only components need are Retrotherm RT, the Retrotherm Reaction Buffer supplied with the enzyme, deoxynucleoside-triphosphates (dNTPs), an RNA template, and specific primers for synthesis of each strand of cDNA. After first-strand synthesis, the RNA:DNA hybrid is thermally denatured to allow the second-strand primer to hybridize to the cDNA for second-strand synthesis in the same buffer. The high reaction temperatures possible with Retrotherm RT minimize secondary structure in templates. Thus, when primers are available for both strands, single-tube cDNA synthesis with Retrotherm RT is easy, fast and powerful, even when working with mixed populations of RNA. Retrotherm RT has no Rnase H activity.

If specific primers are available for priming synthesis of both cDNA strands from a target RNA, then single-tube cDNA synthesis with Retrotherm RT is fast and convenient, even when working with mixed populations of RNA. In these cases, the enzyme's thermostability and its combination of RNA- and DNA-dependent DNA polymerase activities that function well in the same buffer give Retrotherm RT a large advantage over other reverse transcriptases.

The amount of RNA needed depends on the application and whether the sample consists of a single RNA species or a mixture of different RNAs. Similarly, the optimal enzyme concentration will vary with the amount and nature of the template. A typical 50 µl reaction contains 0.5 to 5.0 units of Retrotherm RT. Insufficient enzyme may fail to produce full-length product. Excess enzyme may result in failure to produce discrete bands. Two templates of the same size but differing in sequence, or different amounts of the same template, may have different optimal enzyme concentrations.

RetroAmp™. RetroAmp™ RT DNA Polymerase (Epicentre Technologies), is a highly efficient, thermally stable enzyme. The use of a thermal stable polymerase allows reverse transcription to take place at an elevated temperature, minimizing the effects of RNA secondary structure. RetroAmp™ is available in a commercial preparation with a 10×PCR Enhancer (with betaine) referred to as MasterAmp™. The presence of betaine (trimethyl glycine) in the MasterAmp 10×PCR Enhancer substantially improves the yield and specificity of amplification of many target sequences, especially those containing a high G+C content or secondary structure. Betaine lowers the melting temperature of G+C rich regions to a temperature more similar to A+T(U) rich regions. This results in destabilization of double-stranded regions which limits polymerase pausing, thereby increasing the yield of full-length product. In addition, betaine also may enhance PCR by protecting DNA polymerases from thermal denaturation.

Typically in the RT-PCR reaction, 50 µl reactions are assembled on ice as two separate 25 µl premixes and combined just before the reverse transcription step to minimize RNA sample degradation. One premix includes the dNTPs, primers, and the RNA template. The other premix included all other reaction components. The reactions contain 1×RT-PCR Buffer that comprises 3.0 mM $MgCl_2$, 1× MasterAmp PCR Enhancer, 0.5 mM $MnSO_4$, 400 µM each dNTP, 12.5 pmoles of each primer, 100 ng of total RNA template, and 2.5 units of RetroAmp™ RT DNA Polymerase. Standard reactions are incubated at 60° C. for 20 minutes for first strand cDNA synthesis, followed by 30–35 cycles of PCR. Annealing temperatures vary depending on the primer pair used; typically samples are denatured at 92° C. for 30 seconds, annealed at 60° C. for 30–60 seconds, and extended at 72° C. for 60 seconds. Ten percent of each reaction (5 µl) may be separated by agarose gel electrophoresis and visualized with ethidium bromide staining.

RetroAmp™ RT DNA Polymerase can efficiently reverse transcribe RNA into cDNA at the highest temperatures possible. In the manufacture's specification the ability of RetroAmp™ RT DNA Polymerase to perform high-temperature RT-PCR, is demonstrated by performing RT-PCR using four different first-strand synthesis incubation temperatures (55° C., 60° C., 65° C., and 70° C.) with two different templates. Primers that amplify a 479 bp region of *E. coli* 16S rRNA were used in a standard reaction with the following cycling conditions: RNA was reverse transcribed at the specified temperature for 20 minutes, then 20 cycles of 92° C. for 30 seconds and 68° C. for 60 seconds were performed. Primers that amplify a 250 bp region of the β-actin message from human placental RNA were also used in a standard reaction with the following cycling profile: RNA was reverse transcribed at the specified temperature for 20 minutes, then 35 cycles of 92° C. for 40 seconds and 70° C. for 60 seconds were performed. (These high annealing temperatures were possible because of the primer sequences chosen and the optimized buffer conditions used, including the presence of MasterAmp PCR Enhancer.) The 16S rRNA product is optimally amplified with a reverse transcription temperature of 65° C. and the β-actin message amplifies well under all temperatures tested. The RetroAmp™ RT-PCR produces abundant specific products with reverse transcription temperatures up to 70° C., depending on the primer sequences and template abundance in the reaction.

Thermoscript™ Thermoscript™ (Gibco-BRL) is a new avian reverse transcriptase that has been shown to be useful for high temperature cDNA synthesis to improve RT-PCR (Schwabe et al., Focus, 20: 30–33, 1998). It is cloned RT in which the active site of the RNase H domain has been mutated thereby reducing the RNase H by 99.5% as compared to native AMV. Thermoscript™ is operative in the temperature range between about 50° C. and about 70° C., a description of the efficacy of the Thermoscript™ at this temperature range is given in a FIG. 2 of the product description on the manufacturer' web site. The optimized conditions for first strand synthesis by Thermoscript™ have been described by Schwabe (Schwabe et al., Focus, 20: 30–33, 1998). Briefly, the 20 µl reaction mixture for the synthesis contains 50 mM Tris-acetate (pH 8.4); 75 mM K-acetate; 8 mM Mg-acetate; 5 mM dithioreitol; 1 mM each of dATP, dTTP, dCTP and dGTP; 0.5 µg oligo (dT); 2.5 mg RNA; 40 units RNase inhibitor and 15 units Thermoscript RT. The RT-PCR procedure, total cell RNA and oligo(dT) are incubated at 65° for 5 minutes and cooled on wet ice and cDNA synthesis reaction mixture is added. The reaction tubes are transferred to a prewarmed heating block and incubated for 50 minutes. Following RT inactivation, RNA is degraded by an RNase H. For PCR 20 µl cDNA reaction mixture is added to a 50 µl PCR mixture and incubated for 2 minutes at 94° C. PCR conditions involved 35 cycles of 94° C. for 30 s. 55–60° C. for 30 s. and 68–72° C. for 1 to 15 minutes. Exemplary polymerases used for this method were Platinum Taq™ and eLONGase®.

rTth Reverse Transcriptase. The GeneAmp Thermostable rTth Reverse Transcriptase (Perkin-Elmer) catalyzes the reverse transcription of RNA to cDNA at elevated temperature (60–70° C.) and subsequently amplifies cDNA using the same recombinant thermostable enzyme—rTth DNA Polymerase. The procedure begins with first strand cDNA synthesis from RNA, with rTth DNA Polymerase acting as a reverse transcriptase in the presence of $MnCl_2$ (Myers, T. W. and Gelfand, D. H. *Biochemistry* 30:7661–7666, 1991; Young, et al., *J. of Clinical Microbiology* 31 4:882–886 1993). Subsequently, in the presence of $MgCl_2$, chelating buffer, and the second primer, synthesis of second strand cDNA and amplification of cDNA is initiated.

Reverse transcription using rTth DNA Polymerase is accomplished using a single specific oligonucleotide primer complementary to the 3'-terminus of the RNA. Subsequent PCR amplifications are achieved using specific oligonucleotide primer pairs at intervals progressively 3' to the resultant first-strand cDNA. The reverse transcription is performed at 60° C. for 2 hours, followed by a 1 minute predenaturation step at 95° C. then 40 cycles of 95° C. for 15 s, 65° C. for 30 s, for each primer pair. Starting template can be a poly(A) RNA or RNA from a given tissue with a target copy number of approximately $10^8$ copies. The tissue RNA can be isolated from any desired tissues by techniques well known to those of skill in the art and also by techniques described elsewhere is the specification.

b. DNA Polymerases

Having produced the first strand of the cDNA species using reverse transcription, the present invention also contemplates the use of various DNA polymerases to produce the second strand of the double-stranded cDNA moiety. Exemplary polymerases are described below.

Bst DNA Polymerase, Large Fragment. Bst DNA Polymerase Large Fragment is the portion of the *Bacillus stearothermophilus* DNA Polymerase protein that contains the 5-3 polymerase activity, but lacks the 5-3 exonuclease domain. Bst Polymerase Large Fragment is prepared from an *E. coli* strain containing a genetic fusion of the *Bacillus stearothermophilus* DNA Polymerase gene, lacking the 5-3 exonuclease domain, and the gene coding for *E. coli* maltose binding protein (MBP). The fusion protein is purified to near homogeneity and the MBP portion is cleaved off in vitro. The remaining polymerase is purified free of MBP (Iiyy et al., 1991).

Bst DNA polymerase can be used in DNA sequencing through high GC regions (Hugh and Griffin, *PCR Technology*, 228–229, 1994; McClary et al., *J. DNA Sequencing Mapping*, 1(3): 173–180, 1991) and Rapid Sequencing from nanogram amounts of DNA template (Mead et al., *BioTechniques*, 11(1): 76–87, 1991). The reaction buffer is 1× ThermoPol Butter (20 mM Tris-HCl (pH 8.8 at 25° C.), 10 mM KCl, 10 mM $(NH_4)_2SO_4$, 2 mM $MgSO_4$, 0.1% Triton X-100). Supplied with enzyme as a 10× concentrated stock.

Bst DNA Polymerase does not exhibit 5-3 exonuclease activity. 100 µ/ml BSA or 0.1% Triton X-100 is required for long term storage. Reaction temperatures above 70° C. are not recommended. Heat inactivated by incubation at 80° C. for 10 min. Bst DNA Polymerase cannot be used for thermal cycle sequencing. Unit assay conditions are 50 mM KCl, 20 mM Tris-HCl (pH 8.8), 10 mM $MgCl_2$, 30 nM M13 mp18 ssDNA, 70 nM M13 sequencing primer (–47) 24 mer, 200 µM daTP, 200 µM dCTP, 200 µM dGTP, 100 µM $^3$H-dTTP, 100 µg/ml BSA and enzyme. Incubate at 65° C. Storage buffer is 50 mM KCl, 10 mM Tris-HCl (pH 7.5), 1 mM dithiothreitol, 0.1 mM EDTA, 0.1% Triton-X-100 and 50% glycerol. Storage is at –20° C.

$VENT_R$® DNA Polymerase and $VENT_R$® (exo$^-$) DNA Polymerase. $Vent_R$ DNA Polymerase is a high-fidelity thermophilic DNA polymerase. The fidelity of $Vent_R$ DNA Polymerase is 5-15-fold higher than that observed for Taq DNA Polymerase (Mattila et al., *Nucleic Acid Res*, 19:4967–4973, 1991; Eckert and Kunkel, *PCR Methods and Applications*, 1:17–24, 1991). This high fidelity derives in part from an integral 3-5 proofreading exonuclease activity in $Vent_R$ DNA Polymerase (Mattila et al., *Nucleic Acid Res*, 19:4967–4973, 1991; Kong et al., *J. Biol. Chem.*, 268: 1965–1975, 1993). Greater than 90% of the polymerase activity remains following a 1 h incubation at 95° C.

$Vent_R$ (exo–) DNA Polymerase has been genetically engineered to eliminate the 3-5 proofreading exonuclease activity associated with $Vent_R$ DNA Polymerase (Kong et al., 1993). This is the preferred form for high-temperature dideoxy sequencing reactions and for high yield primer extension reactions. The fidelity of polymerization by this form is reduced to a level about 2-fold higher than that of Taq DNA Polymerase (Mattila et al., *Nucleic Acid Res*, 19:4967–4973, 1991; Eckert and Kunkel, *PCR Methods and Applications*, 1:17–24, 1991.). $Vent_R$ DNA (exo–) DNA Polymerase is a good choice for DNA sequencing.

Both $Vent_R$ and $Vent_R$ (exo–) are purified from strains of *E. coli* that carry the Vent DNA Polymerase gene from the archaea *Thermococcus litoralis* (Perler et al., *Proc. Nat'l Acad. Sci. USA*, 89:5577, 1992). The native organism is capable of growth at up to 98° C. and was isolated from a submarine thermal vent (Belkin and Jannasch, *Arch. Microbiol.*, 141:181–186, 1985). They are useful in primer extension, thermal cycle sequencing and high temperature dideoxy-sequencing.

DEEP $VENT_R$™ DNA Polymerase and DEEP $VENT_R$™ (exo$^-$) DNA Polymerase. Deep $Vent_R$ DNA Polymerase is the second high-fidelity thermophilic DNA polymerase available from New England Biolabs. The fidelity of Deep $Vent_R$ DNA Polymerase is derived in part from an integral 3-5 proofreading exonuclease activity. Deep $Vent_R$ is even more stable than $Vent_R$ at temperatures of 95° C. to 100° C.

Deep $Vent_R$ (exo–) DNA Polymerase has been genetically engineered to eliminate the 3-5 proofreading exonuclease activity associated with Deep $Vent_R$ DNA Polymerase. This exo– version can be used for DNA sequencing but requires different dNTP/ddNTP ratios than those used with $Vent_R$ (exo–) DNA Polymerase. Both Deep $Vent_R$ and Deep $Vent_R$ (exo–) are purified from a strain of *E. coli* that carries the Deep $Vent_R$ DNA Polymerase gene from *Pyrococcus* species GB–D (Perler et al., 1996). The native organism was isolated from a submarine thermal vent at 2010 meters (Jannasch et al., *Applied Environ. Microbiol.*, 58:3472–3481, 1992) and is able to grow at temperatures as high as 104° C. Both enzymes can be used in primer extension, thermal cycle sequencing and high temperature dideoxy-sequencing.

T7 DNA Polymerase (unmodified). T7 DNA polymerase catalyzes the replication of T7 phage DNA during infection. The protein dimer has two catalytic activities: DNA polymerase activity and strong 3-5 exonuclease Hori et al., *J. Biol. Chem.*, 254:11598–11604, 1979; Engler et al., *J. Biol. Chem.*, 258:11165–11173, 1983; Nordstrom et al., *J. Biol. Chem.*, 256:3112–3117, 1981). The high fidelity and rapid extension rate of the enzyme make it particularly useful in copying long stretches of DNA template.

T7 DNA Polymerase consists of two subunits: T7 gene 5 protein (84 kilodaltons) and *E. coli* thioredoxin (12 kilodaltons) (Hori et al. *J. Biol. Chem.*, 254:11598–11604, 1979; Studier et al., *Methods Enzymol.*, 185:60–89, 1990; Grippo and Richardson, *J. Biol. Chem.*, 246:6867–6873, 1971; Modrich and Richardson, *J. Biol. Chem.*, 250:5515–5522, 1975; Adler and Modrich, *J Biol Chem* 254(22):11605–14, 1979). Each protein is cloned and over-expressed in a T7 expression system in *E. coli* (Studier et al., *Methods Enzymol.*, 185:60–89, 1990). It can be used in second strand synthesis in site-directed mutagenesis protocols (Bebenek and Kunkel, *Nucleic Acids Res.* 17(13):5408, 1989).

The reaction buffer is 1×T7 DNA Polymerase Buffer (20 mM Tris-HCl (pH 7.5), 10 mM $MgCl_2$, 1 mM dithiothreitol). Supplement with 0.05 mg/ml BSA and dNTPs. Incubate at 37° C. The high polymerization rate of the enzyme makes long incubations unnecessary.

Unit assay conditions are 20 mM Tris-HCl (pH 7.5), 10 mM $MgCl_2$, 1 mM dithiothreitol, 0.05 mg/ml BSA, 0.15 mM each dNTP, 0.5 mM heat denatured calf thymus DNA and enzyme. Storage conditions are 50 mM $KPO_4$ (pH 7.0), 0.1 mM EDTA, 1 mM dithiotireitol and 50% glycerol. Store at –20° C.

DNA Polymerase I (*E. coli*). DNA Polymerase I is a DNA-dependent DNA polymerase with inherent 3-5 and 5-3 exonuclease activities (Lehman, 1981). The 5-3 exonuclease activity removes nucleotides ahead of the growing DNA chain, allowing nick-translation. It is isolated from *E. coli* CM 5199, a lysogen carrying polA transducing phage (Murray and Kelley, *Molec. Gen. Genet.*, 175:77–87, 1979). The phage in this strain was derived from the original polA phage encoding wild-type Polymerase I.

Applications include nick translation of DNA to obtain probes with a high specific activity (Meinkoth and Wahl, *Methods Enzymol.*, 152:91–94, 1987) and second strand synthesis of cDNA (Gubler and Hoffmann, *Gene*, 25:263–269, 1983; D'Alessio and Gerard, *Nucl. Acids Res.*, 16:1999–2014, 1988). The reaction buffer is *E. coli* Polymerase I/Klenow Buffer (10 mM Tris-HCl (pH 7.5), 5 mM $MgCl_2$, 7.5 mM dithiothreitol).

DNase I is not included with this enzyme and must be added for nick translation reactions. Heat inactivation is for 20 min at 75° C. Unit assay conditions are 40 mM $KPO_4$ (pH 7.5), 6.6 mM $MgCl_2$, 1 mM 2-mercaptoethanol, 20 µM dAT copolymer, 33 µM dATP and 33 µM $^3$H-dTTP. Storage conditions are 0.1 M $KPO_4$ (pH 6.5), 1 mM dithiothreitol, and 50% glycerol. Store at –20° C.

DNA Polymerase I, Large (Klenow) Fragment. Klenow fragment is a proteolytic product of *E. coli* DNA Polymerase I which retains polymerization and 3-5 exonuclease activity, but has lost 5-3 exonuclease activity. Klenow retains the polymerization fidelity of the holoenzyme without degrading 5 termini.

A genetic fusion of the *E. coli* polA gene, that has its 5-3 exonuclease domain genetically replaced by maltose binding protein (MBP). Klenow Fragment is cleaved from the fusion and purified away from MBP. The resulting Klenow fragment has the identical amino and carboxy termini as the conventionally prepared Klenow fragment.

Applications include DNA sequencing by the Sanger dideoxy method (Sanger et al., *Proc. Nat'l Acad. Sci. USA*, 74:5463–5467, 1977), fill-in of 3 recessed ends (Sambrook et al., *In: Molecular Cloning: A Laboratory Manual*, second edition, Cold Spring Harbor Laboratory, Cold Spring Harbor, N.Y., 1989), second-strand cDNA synthesis, random priming labeling and second strand synthesis in mutagenesis protocols (Gubler, *Methods Enzymol.*, 152:330–335, 1987).

Reactions conditions are 1× *E. coli* Polymerase I/Klenow Buffer (10 mM Tris-HCl (pH 7.5), 5 mM $MgCl_2$, 7.5 mM dithiothreitol). Supplement with dNTPs. Klenow fragment is also 50% active in all four standard NEBuffers when supplemented with dNTPs. Heat inactivated by incubating at 75° C. for 20 min. Fill-in conditions: DNA should be dissolved, at a concentration of 50 µg/ml, in one of the four standard NEBuffers (1×) supplemented with 33 M each dNTP. Add 1 unit Klenow per µg DNA and incubate 15 min at 25° C. Stop reaction by adding EDTA to 10 mM final concentration and heating at 75° C. for 10 min. Unit assay conditions 40 mM $KPO_4$ (pH 7.5), 6.6 mM $MgCl_2$, 1 mM 2-mercaptoethanol, 20 µM dAT copolymer, 33 µM dATP and 33 µM $^3$H-dTTP. Storage conditions are 0.1 M $KPO_4$ (pH 6.5), 1 mM dithiothreitol, and 50% glycerol. Store at −20° C.

Klenow Fragment (3-5 exo⁻). Klenow Fragment (3-5 exo−) is a proteolytic product of DNA Polymerase I which retains polymerase activity, but has a mutation which abolishes the 3-5 exonuclease activity and has lost the 5-3 exonuclease (Derbyshire et al. 1988).

A genetic fusion of the *E. coli* polA gene, that has its 3-5 exonuclease domain genetically altered and 5-3 exonuclease domain replaced by maltose binding protein (MBP). Klenow Fragment exo− is cleaved from the fusion and purified away from MBP. Applications include random priming labeling, DNA sequence by Sanger dideoxy method (Sanger et al., *Proc. Nat'l Acad. Sci. USA*, 74:5463–5467, 1977), second strand cDNA synthesis and second strand synthesis in mutagenesis protocols (Gubler, *Methods Enzymol.*, 152: 330–335, 1987).

Reaction buffer is 1× *E. coli* Polymerase I/Klenow Buffer (10 mM Tris-HCl (pH 7.5), 5 MM $MgCl_2$, 7.5 mM dithiothreitol). Supplement with dNTPs. Klenow Fragment exo− is also 50% active in all four standard NEBuffers when supplemented with dNTPs. Heat inactivated by incubating at 75° C. for 20 min. When using Klenow Fragment (3-5 exo−) for sequencing DNA using the dideoxy method of Sanger et al. (Sanger et al., *Proc. Nat'l Acad. Sci. USA*, 74:5463–5467, 1977), an enzyme concentration of 1 unit/5 µl is recommended.

Unit assay conditions are 40 mM $KPO_4$ (pH 7.5), 6.6 mM $MgCl_2$, 1 mM 2-mercaptoethanol, 20 µM dAT copolymer, 33 µM dATP and 33 µM $^3$H-dTTP. Storage conditions are 0.1 M $KPO_4$ (pH 7.5), 1 mM dithiothreitol, and 50% glycerol. Store at −20° C.

T4 DNA Polymerase. T4 DNA Polymerase catalyzes the synthesis of DNA in the 5-3 direction and requires the presence of template and primer. This enzyme has a 3-5 exonuclease activity which is much more active than that found in DNA Polymerase I. Unlike *E. coli* DNA Polymerase 1, T4 DNA Polymerase does not have a 5-3 exonuclease function.

Purified from a strain of *E. coli* that carries a T4 DNA Polymerase overproducing plasmid. Applications include removing 3' overhangs to form blunt ends (Tabor and Struhl, *In: Current Protocols in Molecular Biology*, Ausubel et al. (Eds.), John Wiley and Sons, NY, pp 3.5.10–3.5.12, 1989; Sambrook et al., *In: Molecular Cloning: A Laboratory Manual*, second edition, Cold Spring Harbor Laboratory, Cold Spring Harbor, N.Y., 1989), 5' overhang fill-in to form blunt ends (Tabor and Struhl, *In: Current Protocols in Molecular Biology*, Ausubel et al. (Eds.), John Wiley and Sons, NY, pp 3.5.10–3.5.12, 1989; Sambrook et al., *In: Molecular Cloning. A Laboratory Manual*, second edition, Cold Spring Harbor Laboratory, Cold Spring Harbor, N.Y., 1989), single strand deletion subcloning (Dale et al., *Plasmid*, 13:31–40, 1985), second strand synthesis in site-directed mutagenesis (Kunkel et al., *Methods Enzymol.*, 154: 367–382, 1987). and probe labeling using replacement synthesis (Tabor and Struhl, *In: Current Protocols in Molecular Biology*, Ausubel et al. (Eds.), John Wiley and Sons, NY, pp 3.5.10–3.5.12, 1989; Sambrook et al., *In: Molecular Cloning: A Laboratory Manual*, second edition, Cold Spring Harbor Laboratory, Cold Spring Harbor, N.Y., 1989).

The reaction buffer is 1×T4 DNA Polymerase Buffer (50 mM NaCl, 10 mM Tris-HCl, 10 mM $MgCl_2$, 1 mM dithiothreitol (pH 7.9 at 25° C.)). Supplement with 40 µg/ml BSA and dNTPs. Incubate at temperature suggested for specific protocol.

According to the manufacturer, it is recommended to use 100 µM of each dNTP, 1–3 units polymerase/µg DNA and incubation at 12° C. for 20 min in the above reaction buffer (Tabor and Struhl, *In: Current Protocols in Molecular Biology*, Ausubel et al. (Eds.), John Wiley and Sons, NY, pp 3.5.10–3.5.12, 1989; Sambrook et al., *In: Molecular Cloning: A Laboratory Manual*, second edition, Cold Spring Harbor Laboratory, Cold Spring Harbor, N.Y., 1989). Heat inactivated by incubating at 75° C. for 10 min. T4 DNA Polymerase is active in all four standard NEBuffers when supplemented with dNTPs.

Taq Polymerases. Native Taq™ (Perkin-Elmer) DNA Polymerase is a thermostable, 94-kDa DNA polymerase isolated from *Thermus aquaticus* YT1. It is primarily used for exact replication of studies performed prior to the availability of recombinant AmpliTaq DNA Polymerase. AmpliTaq DNA Polymerase is a 94-kDa, gelatin-free, thermostable, recombinant DNA polymerase obtained by expression of a modified form of the Taq DNA Polymerase gene cloned in *E. coli* (Lawyer, et al., *J. Biol. Chem.* 264:6427–6437, 1989; Lawyer, et al., *PCR Meth. and Appl.* 2(4): 275–287, 1993).

The thermal activity profile of AmpliTaq DNA Polymerase is ideal for PCR applications because its optimal activity is in the same range at which stringent annealing of primers occurs (55° C.–75° C.). The enzyme's PCR cycling half-life is 50 cycles at 95° C., providing sufficient thermostability such that there is no substantial loss of enzymatic activity, even after repeated exposure to the highest temperatures recommended in most PCR protocols. The enzyme has a 5'-3' exonuclease activity which has been exploited in development of a homogeneous simultaneous signal generation assay (Holland, P., et al., *Proc. Natl. Acad. Sci.* USA 88:7276–7280, 1991) and it lacks 3'-5' exonuclease activity.

Tfl DNA Polymerase. Tfl is yet another polymerase enzyme with an apparent molecular weight of approximately 94 kDa. It was isolated from *Thermus flavus* (Kaledin et al., *Biokhimiia*. 46(9): 1576–1584, 1981). The isolated enzyme is thermostable and has a temperature optimum on the DNA templates at 70° C. and that on RNA templates at 50° C. The enzyme does not appear to contain contaminant endo- and exonuclease activities. For maximal activity, the enzyme requires the presence of template, four deoxyribonucleoside triphosphates and monovalent and bivalent cations in the incubation mixture. The enzyme is highly active when "activated" DNA, poly(dA)-poly(dT), poly(dA)-oligo(dT) 10 and poly(rA)-oligo(dT)10 are used as templates, moderately active on single-stranded and double-stranded DNAs and inactive on poly(rC)-oligo(dG)12–18 and native RNA molecules. Tfl is commercially available from a variety of sources including Promega (Madison, Wis.).

Tht DNA Polymerase was isolated from *Thermus thermophilus* HB-8 (Ruttimann et al. *Eur J Biochem.* 149(1): 41–46, 1985). This enzyme catalyzes the DNA polymerization, of nucleotides into duplex DNA in the 5'-3' direction in the presence of $MgCl_2$. Also the enzyme catalyzes RNA polymerization in the presence of $MgCl_2$.

Tli DNA polymerase. Tli DNA polymerase is an extremely thermostable polymerase that replicates DNA at 75° C. and remains functional even after incubation at 100° C. Tli DNA polymerase has an integral 3'-5' exonuclease activity (proofreading) function. The enzyme has a molecular weight of approximately 90 kDa (Mattila et al., *Nucleic Acid Res,* 19:4967–4973, 1991) and is commercially available from a variety of sources.

UlTma DNA Polymerase is a thermostable DNA polymerase specifically designed, thoroughly optimized and tested for its ability to repair 3'-mismatches in PCR amplification, to provide high yield of specific PCR product, and to produce blunt-ended PCR products suitable for cloning and gene expression. UlTma DNA Polymerase, a 70-kDa recombinant enzyme, is encoded by a modified form of a *Thermotoga maritina* DNA polymerase gene which has been cloned and expressed in *E. coli* (U.S. Pat. No. 5,310,652, incorporated herein by reference). The enzyme has been specifically engineered to achieve an optimal balance between polymerase and proofreading activity. It has also been optimized for higher yield by using a hot start reaction.

C. Methods of Diagnosing Disorders

The present invention contemplates using ISRT-PCR to identify any disorder that may be characterized by a gene aberration or expression. The ability to distinguish cells under the microscope possessing the particular characteristic that is diagnostic of the disorder from those cells that do not possess this characteristic.

ISRT-PCR will therefore be useful in the detection/diagnosis of various diseases. For example, this technique may be used to detect low copy number viral infections by infections agents such as HIV, HPV—Human papilloma virus in cervical cancers, CMV—Cytomegalous virus in transplant kidneys, EBV—Epstein Barr virus in lymphomas, Hepatitis B Virus, Hepatitis C virus in cases of post-transfusion hepatitis. Other infectious particles that may be detected include for example *Helicobacter pylori, Leprosy,* and *Tuberclosis.*

In other embodiments, the present invention may be employed to identify chromosomal rearrangements and translocations in a diseased state such as in certain tumors. In these embodiments, the method may be employed to detect immunoglobin heavy and light chain genes, B and T clonality studies, Bcl-2 (t 14:18), Ewings' sarcomas, PNET—Peripheral neuroectodermal tumor and the like.

In still further embodiments, the disorder may be a sclerotic glomerular diseases in which the method is employed to detect Type IV Collagen (α2IV collagen mRNA) in nephrectomy specimens from renal carcinoma patients, metalloproteinase mRNAs in prognosis of cervical carcinoma, single copy Ig gene rearrangements in human B lymphocytes, HLA-DQ haplocytes in human peripheral blood mononuclear cells.

Histoplasmosis in granuloma cells also may be detected by the ISRT-PCR methods of the present invention. For example, BRCA1 can be detected in early onset in breast carcinoma, breast-ovarian cancer and proliferative breast disease; BRCA2 is an additional marker for certain breast cancers; and the presence of MSH 2 and MLH 1 is indicative of colon cancer.

Of course it should be understood that the present invention could be employed to detect any tumor marker that may be present on a cell. Tumor cells have a wide variety of markers, including the defined expression of cancer-specific antigens such as Muc 1, HER-2 and mutated p53 in breast cancer.

Burkitt lymphoma results from chromosome translocations that involve the Myc gene. Thus changes in the pattern of Myc expression, that disrupt its usual function in controlling cell growth and proliferation can be detected by the methods described herein.

MEN1 gene, involved in multiple endocrine neoplasia, has been known for several years to be found on chromosome 11, may serve as a marker for endocrine cancers. Adenocarcinoma of the colon has defined expression of CEA and mutated p53, both well-documented tumor signatures.

From the discussion above it becomes clear that there are many different tumor markers some of which are specific to a particular type of cancer and others which are promiscuous in their origin. Those of skill in the art will generally know of the variety of signatures that may be indicative of a particular cancer. Some of the more common tumor suppressors that may act as cancer markers for the present invention include but are not limited to Muc 1, CCAM, RB, APC, DCC, MEN-I, MEN-II, zac1, MMAC1, FCC, MCC p16, p21, p27, p53, p73, zac1, MMAC1, Rb, Wilms tumor (WT-1), DCC, neurofibromatosis type 1 (NF-1), NF-2, von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS ¼ pan-carcinoma antigen, ovarian carcinoma antigen (CA125), prostate specific antigen, melanoma antigen gp75, CD9, CD63, CD53, CD37, CD63, R2, CD81, CO029, Tl-1, L6 and SAS (Wright and Tomlinson, 1994). Of course these are merely exemplary tumor suppressors and it is envisioned that the present invention may be used in conjunction with any other agent that is or becomes known to those of skill in the art as a tumor suppressor.

Further, particularly the invention could identify a selected oncogene. These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

It is contemplated that the moiety is a tumor specific antigen such as for example, carcinoembryonic antigen, prostate specific antigen, tyrosinase, ras, a sialyly lewis antigen, erb, MAGE-1, MAGE-3, BAGE, MN, gp100, gp75, p97, a mucin, CD81, CD9, CD63; CD53, CD38, CO-029, CA125, GD2, GM2 and O-acetyl GD3, M-TAA, M-fetal or M-urinary.

Thus, the cell proliferative disorders, or cancers, contemplated to be detectable with the methods of the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oilodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera. lymphoma (Hodgkin's disease and non-Hodgkin's disease), multiple myeloma, Waldenstrbm's macroglobulinemia, and heavy chain disease.

D. Primers and Probes

The present invention will employ various primers and probes for initiating the synthesis of cDNA moieties from a cell. Also, PCR primers may be designed for specific genes and are used to determine whether the particular genes is represented in the cells tested in the present invention.

a. Primer Design

The term primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

The particular length of the primer is not believed to be critical, with the dT sequence ranging from about 10 to about 25 bases, with 11 being a preferred embodiment. In some embodiments, the primers are labeled with radioactive species ($^{32}P$, $^{14}C$, $^{35}S$, $^{3}H$, or other isotope), with a fluorophore (rhodamine, fluorescein, GFP) or a chemiluminescent label (luciferase).

b. Probes

In various contexts, it may be necessary to use oligo or polynucleotides as probes for complementary or hybridizing DNA or RNA molecules. In this regard, one may include particular "target" sequences in the oligo's of the present invention in order to detect the products by probe hybridization. Alternatively, the probes may recognize unique sequences in the amplified regions upstream of the oligo-dT primers.

c. Hybridization

Suitable hybridization conditions will be well known to those of skill in the art. Typically, the present invention relies on high stringency conditions (low salt, high temperature), which are well known in the art. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

d. Primer Synthesis

Oligonucleotide synthesis is performed according to standard methods. See, for example, Itakura and Riggs (Itakura and Riggs, Science 209:1401–1405, 1980). Additionally, U.S. Pat. No. 4,704,362; U.S. Pat. No. 5,221,619 U.S. Pat. No. 5,583,013 each describe various methods of preparing synthetic structural genes.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester method. The diester method was the first to be developed to a usable state, primarily by Khorana and co-workers. (Khorana, Science 203, 614 1979). The basic step is the joining of two suitably protected deoxynucleotides to form a dideoxynucleotide containing a phosphodiester bond. The diester method is well established and has been used to synthesize DNA molecules (Khorana, Science 203, 614 1979).

Triester method. The main difference between the diester and triester methods is the presence in the latter of an extra protecting group on the phosphate atoms of the reactants and products (Itakura et al., J. Biol. Chem. 250, 4592 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligodeoxynucleotides (Gillam et al., J. Biol. Chem. 253, 2532, 1978; Gillam et al., Nucleic Acids Res. 6, 2973, 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage, and Lyer, *Tetrahedron*, 48:2223–2311, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

E. Kits

All the essential materials and reagents required for performing ISRT-PCR according to the present invention may be assembled together in a kit. Such kits generally will comprise preselected primers and may include other oligo- and polynucleotides, such as probes. Also included may be enzymes suitable for amplifying nucleic acids including various polymerases (endonucleases, reverse transcriptases, Taq, Sequenase™, etc.), dNTPs and buffers to provide the necessary reaction mixture for amplification. Such kits also generally will comprise, in suitable means, distinct containers for each individual primer, probe, vector, dNTPs, buffer and enzyme(s).

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials:

Paraformaldehyde was purchased from Sigma (St. Louis, Mo.). Probe-on plus slides were purchased from Fisher Scientific (Itasca, Ill.). Proteinase K. Tritirachium Albium was purchased from Amresco (Solon, Ohio). RNase-free DNase I and Biotin-16-dUTP were purchased from Boehringer Mannheim (Indianapolis, Ind.). RQI-DNase, RNAsin, dNTPS and restriction enzymes were purchased from Promega Scientific Co. (Madison, Wis.). Cy-5 conjugated streptavidin was purchased from Jackson ImmunoResearch Labs (West Grove, Pa.). Primers were synthesized by Operon Technologies (Alameda, Calif.). Superscript II RT enzyme kit was purchased from Gibco-BRL (Rockville, Md.) and AmpliTaq DNA polymerase was purchased from PE Biosystems (Foster City, Calif.).

Methods:

Tissue Fixation. Whole embryonic kidneys or adult murine kidney sections were washed in cold RNase-free PBS. Tissues were fixed in 4% paraformaldehyde-sucrose at 4° C. for 18 hours. Fixed tissues were mounted in OCT compound (Polysciences, Warrington, Pa.) and five to seven micron cryosections were mounted and placed onto RNase-free Probe-On Plus Slides (Fisher Scientific, Itasca, Ill.). The slides were kept at −80° C. until used for direct in situ RT-PCR.

Tissue Processing. Prior to Proteinase K digestion, tissue sections were incubated for 10 seconds at 105° C. on a heat block to ensure tissue adhesion to the slides. The slides were then immersed at room temperature for 27 minutes in Proteinase K solution at a final concentration of 6.66 µg/ml. Tissue digestion conditions were standardized by performing digestions in graded concentrations of Proteinase K for a fixed time. For standardization of digestion conditions, the highest concentration of the enzyme, which did not change the histoarchitecture of the renal tubules, was used. Initially, digestions were monitored under light microscope at 2–3 minute intervals until an optimal digest time was achieved. Enzyme digestions were stopped by incubating the slide for 2 minutes at 105° C. on a heat block. Samples were rinsed briefly, first in PBS and subsequently in DEPC treated water. The slides were air-dried.

After Proteinase K treatment, the genomic DNA in each sample was digested in situ using a humidified chamber at 37° C. for 3 hours with 10–20 units of Sau 96 I alone or in combination with a tetra-cutter enzyme (e.g. Hac III or Hpa II) in universal buffer containing 10 U of RNAsin in a total volume of 20 µl. The slides were washed for 10 seconds each in PBS and DEPC treated water. To ensure complete digestion of genomic DNA in the tissue sections, samples were incubated overnight in a humidified chamber at 37° C. with 10 U of RNase-free DNase (1 U/µl final concentration). The slides were then rinsed twice for 10 seconds each with DEPC treated water.

In situ reverse transcriptase reaction Tissue sections were overlaid with 10 µl of RT mix, 1× $1^{st}$ Strand Buffer (Gibco-BRL, Rockville, Md.) 1 mM each of dATP, dCTP, dGTP and dTTP, 10 U of RNAsin, 6 mM DTT, 0.5 µM of 3'-primer and 5 U of Superscript II RT enzyme (Gibco-BRL) and incubated at 42° C. in a humidified chamber for 1 hour. Reverse transcriptase was omitted from the RT mix for RT minus control slides. Reverse transcription reaction was stopped by incubating the slides for 2 min at 92° C. in a MJR PTC-100 thermal cycler (MJ Research, Watertown, Mass.) fitted with a slide holder. The coverslips were removed and samples washed twice with DEPC treated water.

In situ polymerase chain reaction For amplification of the target krtk (tyro 3) sequence, PCR was carried out in situ on the sections using MJR's PTC-100 thermal cycler. Slides were kept at 4° C. prior to the start of the PCR reaction. 10–20 µl of PCR mix was overlaid on the sections and the slide was sealed with adhesive coverslips (Sigma. St. Louis, Mo.). Two protocols were used, both of which labeled kidney sections specifically with equivalent efficacy. In the first method, reactions were performed in the presence of 1× GeneAmp PCR Buffer containing 1.5 mM $MgCl_2$ (PE Biosystems, Foster City, Calif.), 0.25 mM dNTP, 1.25 µM 5' forward and 3' reverse primer and 0.125 U of AmpliTaq DNA polymerase. The 5' primer was conjugated to Cy-5. In the second approach, reaction conditions were the same except biotin conjugated dUTP was added at a concentration of 0.05 mM and unconjugated 5' primer was used instead of Cy-5 conjugated primer.

PCR mix was added to the center of coverslips (Probe-Clip Press-Seal Incubation Chamber) as spherical droplets and tissue sections were placed over the droplet. The chamber consists of a self-sealing silicone gasket along the circumference of the coverslip. Better sealing was ensured with a colorless nail polish. Cycling reactions were done using hot start conditions by warming the slide holders of 90° C. prior to placing the glass slides in the slide holders for cycling. PCR was carried out for 1 cycle at 92° C. for 90 seconds followed by 30 cycles with denaturation at 94° C. for 30 seconds, annealing at 50° C. for 1 minute and extension at 72° C. for 1 minute. When the polymerase chain reaction was complete, samples were kept at 4° C. Coverslips were removed and the samples were heated to 92° C. for 1 minute. Subsequently, slides were soaked for 5 minutes in 1×PBS at room temperature and counterstained with hematoxylin. Alternatively, in samples where biotin conjugated dUTP was used for labeling, the specimens were incubated at room temperature for 30 minutes with 1 µg/ml of Cy-5 conjugated streptavidin. Then samples were washed twice for 2 minutes at room temperature in 1×PBS and then counterstained with hematoxylin. Samples were overlaid with Permount (Fisher Scientific, Itasca, Ill.) and covered with coverslips.

Light Microscopy Samples were imaged with a Zeiss LSM 510 confocal microscope equipped with Ar and He/Ne lasers. Samples were excited at 633 nm light and images collected with a 650 nm emission filter in the light path. All images were collected using standardized laser intensities and photomultiplier tube settings for amplification and dark levels. All images were processed with Adobe Photoshop on a Micron Millennium computer. Photomicrographs were printed on Kodak XLS 8500 dye sublimation printer.

Example 2

Krtk, an Alternatively Spliced Tyro 3 Isoform is Preferentially Expressed in Proximal Tubules Genes responsible for the development and functional diversity of tubular epithelia along the nephron have not been identified. Differential display PCR was employed to identify genes that are differentially expressed in proximal versus distal tubule cells. Mouse S1 (proximal tubule) and DCT (distal tubule) cell mRNA, was the source mRNA used in differential display PCR. Sequence analysis of a differentially displayed band (334 bp) derived from S1 cells identified the fragment as krtk.

Blast search revealed significant homology to murine tyro 3, belonging to the Axl/Ufo family. Tyro3 is predominantly expressed in adult brain and is an imporimprove RT-PCRant differentiation factor involved in cell adhesion. Krtk (tyro 3) message was detected by RT-In situ PCR in S-shaped bodies and our results demonstrate that Krtk expression is a late developmental event in proximal tubule formation. Conversely, krtk was weakly expressed in distal tubule segments. Northern hybridization analysis with the 334 bp fragment of krtk (3'-end) showed a 4.4 kb transcript.

Hybridizations with krtk 5' regions reveal two novel transcripts of 6.0 kb, and 3.8 kb besides the previously described 4.4 kb transcript. A 50-fold enrichment of the 3.8 kb transcript in S1 cells as compared to DCT cells was observed by Northern blot. Therefore krtk is differentially expressed and alternatively spliced in kidney (FIGS. 1A–E).

Figures 2A, 2B, 2C, 2D, 2E, 2F, 2G:
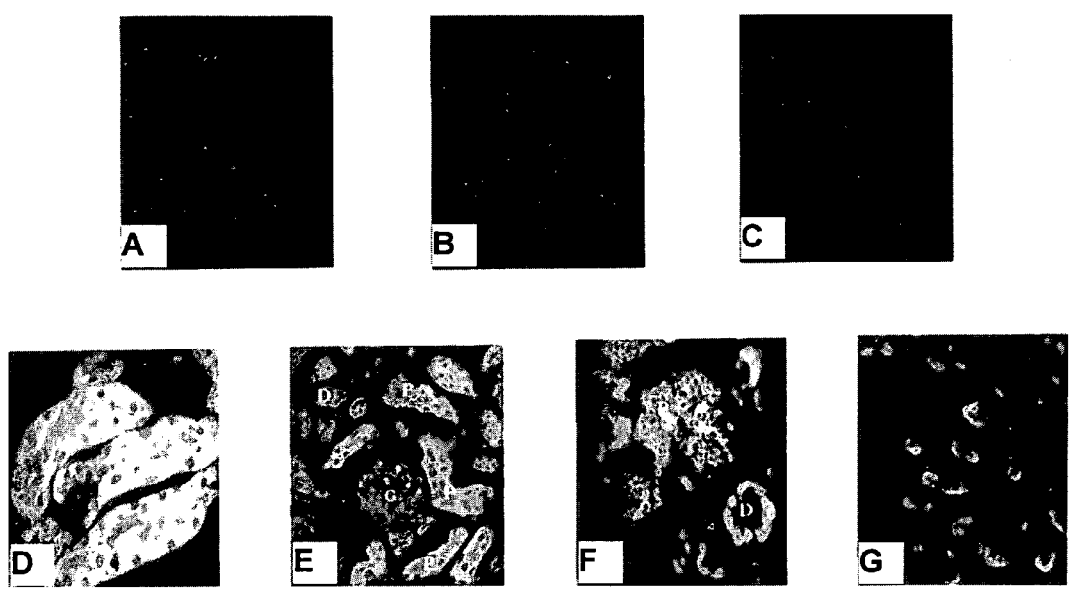
FIGS. 2A through 2G. Direct in situ RT-PCR in Murine Kidney.

To determine the spatial distribution of krtk in tissue sections, a direct label RT-PCR method was developed utilizing fluorescent labels which permit direct visualization of transcript expression by light microscopy. This method was optimized to achieve the highest possible signal to noise ratio between negative controls and samples containing RNA transcripts. An important feature of the negative control images was the utilization of Cy-5 as the fluorophore. In preliminary experiments, significant autofluorescence was observed when samples were imaged with filter sets optimized for fluorescein, or rhodamine fluorescence (FIG. 2A). At increasingly red-shifted excitation wavelengths, less autofluorescent signal was detected. Using filter sets optimized for Texas Red or Cy-3, a detectable emission signal was still noted in unstained kidney sections. However, no detectable image was seen using Cy-5 filter sets. This led to a dramatic improvement in the signal to noise ratio.

In FIG. 2, expression of krtk (tyro3) in murine kidney sections is shown. Little staining is noted in samples imaged without a reverse transcriptase reaction (FIG. 2B). When the in situ PCR reaction was performed without one of the printers or Taq polymerase, no staining was detectable (FIG. 2C). In contrast, when direct in situ PCR was performed with all necessary enzymes, reverse transcriptase and Taq polymerase, diffuse cytoplasmic staining is observed in proximal tubule segments (FIGS. 2D and 2E). Note however that the nuclear compartment is relatively devoid of staining. These samples were treated with a tetra-cutting DNA restriction enzyme, Sau 96 I and subsequently with RNase free DNase I. In tissue samples in which the restriction enzyme digestions were omitted, significant additional fluorescent signals were detected both in the nuclear compartment and in the cytoplasm, suggesting that genomic DNA contributed to the images. This effect is demonstrated in samples labeled with primers for GAPDH.

In FIG. 2F, the expression of GAPDH is cytoplasmic in the restriction and DNase I digested sample. In contrast, samples that were digested with DNase I alone had significant fluorescent signal in the nucleus and cytoplasm (FIG. 2G). In samples treated with a tetracutter restriction enzyme and subsequently with RNase-free DNase I, but reverse transcriptase was omitted, no signal was detected (FIG. 2B). The use of this control confirms that no genomic amplification takes place in the samples.

It will be clear that the invention may be practiced otherwise than as particularly described in the foregoing description and examples. Numerous modifications and variations of the present invention are possible in light of the above teachings and, therefore, are within the scope of the invention. The disclosures of all publications cited herein are hereby incorporated by reference.

The invention claimed is:

1. A method for in situ amplification and detection of a target nucleic acid sequence in a fixed, permeabilized cell comprising:
   (a) selecting a forward and a reverse primer for said target nucleic acid, wherein the forward and reverse primers flank at least one restriction enzyme site within said target nucleic acid sequence;
   (b) contacting the fixed, permeabilized cell with a restriction endonuclease composition comprising at least one restriction endonuclease that cuts a genomic nucleic acid sequence flanked by the forward and reverse primers specific for said target nucleic acid, to produce a restriction digest;
   (c) contacting said restriction digest in the cell with a DNAse to produce a DNAse digested cell;
   (d) incubating said cell with a reverse transcriptase (RT) cocktail comprising an RT enzyme and a RT primer specific for said target nucleic acid to produce a cDNA; and (e) amplifying said cDNA using a PCR reaction in the presence of the forward and reverse primers wherein at least one of said forward and reverse primers is labeled; and (f) detecting the amplified cDNA.

2. The method of claim 1, wherein at least one of said primers is labeled with a radioactive label, an immunocytochemical label or a fluorescent label to facilitate detection of said amplified cDNA.

3. The method of claim 2, wherein at least one of said primers is labeled with a fluorescent label that fluoresces in the far red range of fluorescence range.

4. The method of claim 3, wherein said fluorescent label fluorescent label fluoresces at about 545 nm or higher.

5. The method of claim 3, wherein said fluorescent label fluoresces at about 645 nm or higher.

6. The method of claim 3, wherein said label is selected from the group consisting of Cy-5, Cy-3, rhodamine and Texas Red.

7. The method of claim 1, wherein said primer is labeled with biotin and digoxigenin.

8. The method of claim 1, wherein said restriction endonuclease composition comprises one or more tetra-cutter restriction endonucleases.

9. The method of claim 1, wherein said restriction endonuclease composition comprises one or more restriction endonucleases selected from the group consisting of Hae III, Hpa II, Mbo I, Cfo I Hha I, and Bst 98 I.

10. The method of claim 1, wherein said DNAse is DNAse I.

11. The method of claim 1, wherein said cell has been permeabilized by contacting said cell with proteinase selected from the group consisting of trypsinase, pepsinogen, and proteinase K.

12. The method of claim 1, wherein said reverse transcriptase is selected from the group consisting of Superscript™; AMV Reverse Transcriptase, M-MLV Reverse Transcriptase, Rethrotherm™; Thermoscript™ and Tth reverse transcriptase.

13. The method of claim 1, wherein said fixed, permeabilized cell is in a tissue sample selected from the group consisting of kidney, heart, lung, liver, blood, pancreas, cervix, breast and muscle.

14. The method of claim 13, wherein said tissue sample has been obtained from a subject.

15. The method of claim 14, wherein said subject is suffering from a disease selected from the group consisting of cancer, cystic fibrosis, cardiac hypertrophy, and autoimmune diseases.

16. The method of claim 1, wherein said fixed, permeabilized cell is a tumor cell.

17. The method of claim 1, wherein said target nucleic acid encodes a marker for an infectious particle.

18. The method of claim 17, wherein said infectious particle is a viral particle selected from the group consisting of hepatitis A, hepatitis B, hepatitis C, HIV 1, HIV 2, and Epstein-Barr virus particles.

19. The method of claim 17, wherein said infectious particle is *M tuberculin,* or *M avian.*

20. The method of claim 17, wherein said target nucleic acid is a disease specific nucleic acid.

21. The method of claim 20, wherein said target nucleic acid is selected from the group consisting of Mucl, CCAM, RB, APC, DCC, MEN-I, MEN-II, zac1, MMAC1, FCC, MCC p16, p21,p27, p53, p73, Rb, WT-1, NF-1, NF-2, BRCA-1, BRCA-2, NITS, CA125, prostate specific antigen, melanoma antigen gp75, CD9, CD63, CD53, CD37, R2, CD81, C0029, TI-1, L6 and SAS.

22. The method of claim 1, wherein said cells have been fixed in a fixative selected from the group consisting of formaldehyde, formalin, paraformaldehyde and glutaraldehyde.

23. The method of claim 1, wherein said fixed, permeabilized cells are located in a histochemical section affixed to a microscope slide.

24. The method of claim 1, wherein said amplifying employs a DNA polymerase selected from the group consisting of DNA Polymerase I, T4 DNA Polymerase, DNA Polymerase I Klenow fragment, PLATINUM taq™, Tfl DNA Polymerase, Taq DNA Polymerase, Tli DNA Polymerase, Tth DNA Polymerase, Vent™, Deepvent™ and pfu.

25. The method of claim 1, wherein said cell comprises between about 0.1 picograms and 10 micrograms of poly (A)+RNA.

26. The method of claim 1, wherein said cell comprises between 1 and 108 copies of said poly(A)+RNA.

27. The method of claim 1, further comprising the step of counterstaining said cell with a non-fluorescent dye.

28. The method of claim 1, wherein one of said forward and reverse PCR primers is the same as said RT primer.

29. A method for in situ amplification and detection of a target nucleic acid sequence in a fixed, permeabilized cell comprising:

(a) selecting a forward and a reverse primer for said target nucleic acid, wherein the forward and reverse primers flank at least one site for restriction enzyme Sau 961 within said target nucleic acid sequence;

(b) contacting a the fixed, permeabilized cell with a restriction endonuclease composition comprising Sau 961 that cuts a genomic nucleic acid sequence flanked by a forward and a reverse primer specific for said target nucleic acid to produce a restriction digest;

(c) contacting said restriction digest with a DNAse to produce a DNase digested cell;

(d) incubating said DNase digested cell with a reverse transcriptase (RT) cocktail comprising an RT enzyme and a RT primer specific for said target nucleic acid to produce a cDNA; and (e) amplifying said cDNA using a polymerase chain reaction (PCR) reaction in the presence of the forward and reverse primers specific for said target nucleic acid wherein at least one of said forward and reverse primers is labeled to facilitate detection wherein contacting the cell with a restriction endonuclease composition produces an increased signal for detection as compared to an in situ RT PCR reaction conducted in the absence of said restriction endonuclease composition.

30. The method of claim 29, wherein said restriction endonuclease composition comprises a further restriction endonuclease selected from the group consisting of Hae III, Hpa II, Mbo I, Cfo I Hha I, and Bst 98 I.

31. A method for improving the signal from in situ RT PCR reaction comprising selecting a forward and a reverse primer for said target nucleic acid, wherein the forward and reverse primers flank at least one restriction enzyme site within said target nucleic acid sequence; then subjecting the target cell to a restriction endonuclease reaction that cuts a genomic nucleic acid sequence flanked by a forward and a reverse PCR primer specific for said target nucleic acid and then digesting with DNase.

32. In a method for carrying out an in situ RT PCR of a target nucleic acid on a fixed cell, the improvement comprising the steps of:
  (a) selecting a forward and a reverse primer for said target nucleic acid, wherein the forward and reverse primers flank at least one site for restriction enzyme Sau 961 within said target nucleic acid sequence;
  (b) contacting the fixed cell with a restriction endonuclease composition that cuts a genomic nucleic acid sequence flanked by a forward and a reverse PCR primer specific for said target nucleic acid to produce a restriction digest, and
  (c) contacting the fixed cell with a DNase composition to produce a DNase digest.

33. The method of claim 32 further comprising the step of conducting the PCR reaction in the presence of at least one PCR primer labeled with a fluorescent label that fluoresces in the far red range of fluorescent range.

34. The method of claim 1, wherein the restriction endonuclease cuts the target nucleic acid more than once.

35. The method of claim 1, wherein more than one restriction endonucleases cut the target nucleic acid.

* * * * *